(12) United States Patent
Bombardelli et al.

(10) Patent No.: US 9,192,636 B2
(45) Date of Patent: Nov. 24, 2015

(54) **COMPOSITIONS COMPRISING *ANDROGRAPHIS PANICULATA* EXTRACTS COMBINED WITH *GINKGO BILOBA* EXTRACTS COMPLEXED WITH PHOSPHOLIPIDS, AND THEIR USE**

(75) Inventors: Ezio Bombardelli, Groppello Cairoli (IT); Andrea Giori, Milan (IT)

(73) Assignee: INDENA S.P.A., Milan (IT)

( * ) Notice: Subject to any disclaimer, the term of this patent is extended or adjusted under 35 U.S.C. 154(b) by 151 days.

(21) Appl. No.: 13/520,154

(22) PCT Filed: Jan. 3, 2011

(86) PCT No.: PCT/EP2011/050016
§ 371 (c)(1),
(2), (4) Date: Aug. 7, 2012

(87) PCT Pub. No.: WO2011/086007
PCT Pub. Date: Jul. 21, 2011

(65) Prior Publication Data
US 2012/0301560 A1    Nov. 29, 2012

(30) Foreign Application Priority Data
Jan. 12, 2010 (IT) .............................. MI2010A0019

(51) Int. Cl.
*A61K 36/16* (2006.01)
*A61K 36/19* (2006.01)
*A61K 36/185* (2006.01)

(52) U.S. Cl.
CPC ................. *A61K 36/16* (2013.01); *A61K 36/19* (2013.01)

(58) Field of Classification Search
None
See application file for complete search history.

(56) References Cited

U.S. PATENT DOCUMENTS

| 2006/0063831 A1* | 3/2006 | Hancke Orozco et al. ... 514/473 |
| 2008/0081046 A1 | 4/2008 | Olalde |

FOREIGN PATENT DOCUMENTS

| EP | 1 559 430 A1 | | 8/2005 |
| JP | 2007028921 A | * | 2/2007 |
| JP | 2010126462 A | * | 6/2010 |
| WO | 03/080062 A1 | | 10/2003 |
| WO | 2005/074953 A1 | | 8/2005 |
| WO | WO2006009464 A2 | * | 1/2006 |
| WO | WO 2009023918 A1 | * | 2/2009 |
| WO | WO2009023918 A1 | * | 2/2009 |

* cited by examiner

*Primary Examiner* — Chris R Tate
*Assistant Examiner* — Randall Winston
(74) *Attorney, Agent, or Firm* — Silvia Salvadori, P.C.; Silvia Salvadori

(57) ABSTRACT

The present invention relates to compositions comprising *Andrographis paniculata* extracts combined with *Ginkgo biloba* extracts complexed with phospholipids.
Moreover, the compositions administered in oils rich in ω-3 polyunsaturated fatty acids demonstrate a further synergic effect between the ingredients.
Said compositions are useful in the treatment of neurodegenerative disorders, in particular Alzheimer's disease and multiple sclerosis.

11 Claims, No Drawings

COMPOSITIONS COMPRISING *ANDROGRAPHIS PANICULATA* EXTRACTS COMBINED WITH *GINKGO BILOBA* EXTRACTS COMPLEXED WITH PHOSPHOLIPIDS, AND THEIR USE

This application is a U.S. National Stage of PCT/EP2011/050016 filed Jan. 3, 2011, which claims priority to and the benefit of Italian Application No. MI2010A000019 filed Jan. 12, 2010, the contents of which applications are incorporated herein by reference in their entirety.

TECHNICAL FIELD OF INVENTION

The present invention relates to compositions containing *Andrographis paniculata* extracts combined with *Ginkgo biloba* extracts complexed with phospholipids, which are useful in the treatment of neurodegenerative disorders, in particular Alzheimer's disease and multiple sclerosis.

PRIOR ART

Disorders such as Alzheimer's disease and multiple sclerosis have a multifactorial etiology. In particular, autoimmune problems and vascular inflammation problems can be identified among the causes of onset of both disorders, which lead to degeneration of areas of the brain.

Said degeneration results in memory loss and loss of peripheral functions.

These disorders are growing rapidly worldwide because of the fast increase in average life expectancy, especially in the industrialised countries.

Alzheimer's disease is the most common cause of dementia in the industrialised countries. It affects around 10% of the population aged over 70, leading to marked loss of memory. This means that 8-10 million individuals are affected in the Western world.

Clinically, Alzheimer's disease presents at the initial stages with memory loss, which worsens over the years until it evolves to marked senile dementia with loss of cognitive, and often functional, capacity.

From the pathological standpoint, diffuse atrophy of the cerebral cortex is observed in the brain, with enlargement of the sulci and ventricles and formation of extracellular plaques containing β-amyloid (Ab). Moreover, the accumulation of this protein in the arterial walls of the cerebral vessels causes their occlusion, leading to atrophy of the affected parts.

The basis for these degenerations, associated with some recently identified genes, is diffuse vascular inflammation which catalyses the modification processes described above.

As regards the treatments currently available, the products used are comprising compounds with anti-acetylcholinesterase activity such as tacrine, donepezil, a physostigmine derivative, and galantamine. However, although the initial effect of these products is favourable, doubts remain as to their effectiveness over time.

Alternative proposals are the use of oestrogens, which are apparently able to modify the progress of the disease in women, and the use of non-steroidal anti-inflammatory drugs, but in both cases the efficacy data are conflicting.

Further attempts with selective vaccinations have not given good results.

Moreover, the above-mentioned products present serious toxicity problems if their dose is increased.

Recent attempts to treat Alzheimer's disease clinically with products of natural origin, such as products comprising *Ginkgo biloba*, which gave encouraging results in preliminary studies, subsequently proved ineffective, probably due to their administration in inadequate doses and/or low absorption of the active ingredients.

Among the active ingredients present in *Ginkgo biloba*, diterpenes and sesquiterpenes, such as bilobalide and ginkgolides, have been identified as compounds potentially useful in the treatment of neurodegenerative disorders, but none of them has reached the clinical phase for these therapeutic purposes.

*Ginkgo biloba* extracts alone had proved to possess beneficial effects on the brain dysfunctions associated with Alzheimer's disease and senile dementia, and a significant contribution to the activity of the extracts was attributed to bilobalide (Sasaki et al. Life science, 67, 709-15, 2000); the use of *Ginkgo biloba* extracts to treat brain disorders was also known by Kidd PM (Alternative medicine, 4, 144-61, 1999), who also reported its use mixed with phosphatidylserine.

Mixtures of *Ginkgo biloba* extracts with phosphatidylserine are present on the US market in the form of "dietary supplements", designed to increase the cognitive functions and prevent Alzheimer's disease (U.S. Pat. No. 6,572,899—JP 2003 169632 A—J. Geriatric and Neurology 11, 163-73, 1998). Controlled trials have not confirmed the desired therapeutic efficacy, so different technological and therapeutic approaches are required to obtain good results.

It is known that when *Ginkgo biloba* extracts are complexed with phospholipids, there is an increase in the bioavailability of the chemical species of the extracts considered to be the active ingredients. The absorption of the active ingredients and an adequate concentration thereof in the brain is extremely important in the treatment of disorders of that organ.

Recently, in WO 2005/074956 and Human Psychopharmacology 22, 1999-2010, 2007, it was demonstrated that the administration of *Ginkgo biloba* complex with phospholipids, in particular with phospholipids containing 10 to 50% of phosphatidylserine, is active in the treatment and prevention of disorders connected with a reduction in cognitive capacity, such as senile dementia and Alzheimer's disease.

EP 0 441 297 B1 discloses the complex of bilobalide with phospholipids, including phosphatidylserine, which demonstrates a marked anti-inflammatory effect when administered topically or systemically.

More recently it was reported that administration of *Ginkgo biloba* complexes with phospholipids leads to the detection of far higher amounts of active ingredients in the brain than administration of the uncomplexed form (Rossi R. et al., J. Pharmaceutical and Biomedical Analysis, 50, 224-27, 2009).

WO 2005/074953 discloses labdane diterpene compositions extracted from *Andrographis paniculata*, which are useful in the treatment of autoimmune diseases and Alzheimer's disease.

Not all the mixtures described in the literature and present on the market fully satisfy the therapeutic requirements. There is consequently a need to identify new compositions which are effective in the treatment of neurodegenerative disorders, in particular Alzheimer's disease and multiple sclerosis, and take account of different effects, such as the immunomodulating, anti-inflammatory and vasokinetic effects.

As the pathogenesis of neurodegenerative disorders is complex and multifactorial, it is clear that a single active ingredient is unlikely to modify their progress; combinations of extracts are therefore needed which, for different reasons, can act on a number of the trigger factors of these disorders, so as to reduce their progress.

SUMMARY OF THE INVENTION

The present invention relates to a composition comprising:
(a) an extract of *Andrographis paniculata* or pure andrographolide,
(b) an extract of *Ginkgo biloba* complexed with phospholipids.

The present invention also relates to the use of a composition comprising:
(a) an extract of *Andrographis paniculata* or pure andrographolide,
(b) an extract of *Ginkgo biloba* complexed with phospholipids, for the treatment of neurodegenerative disorders, in particular Alzheimer's disease and multiple sclerosis.

DETAILED DESCRIPTION OF THE INVENTION

It has now surprisingly been found that compositions obtained by combining *Andrographis paniculata* extracts with *Ginkgo biloba* extracts complexed with phospholipids, are useful in the treatment of neurodegenerative disorders, in particular Alzheimer's disease and multiple sclerosis.

The present invention relates to a composition comprising:
(a) an extract of *Andrographis paniculata* or pure Andrographolide,
(b) an extract of *Ginkgo biloba* complexed with phospholipids.

*Andrographis paniculata* extract is preferably prepared from the aerial parts of the fresh or dehydrated plant by extraction of the biomass with alcohols miscible with water, preferably with ethanol, or, depending on the starting plant material, with ketones and/or aliphatic esters and ethers. After concentrating the primary extracts to a small volume under vacuum, the residues are distributed between water and immiscible solvents to concentrate the active ingredient, andrographolide, selectively until the desired concentrations in the final extract are reached.

*Andrographis paniculata* extract preferably contains andrographolides (such as andrographolide, 14-deoxy-11, 12-didehydroandrographolide and neo-andrographolide) from 20% to 60%, and more preferably 35%.

Moreover, according to another aspect of the invention, pure andrographolide, obtainable according to known processes, can be used for particular formulations, although extracts enriched with *Andrographis paniculata* are particularly preferred, because they supply the best bioavailability and activity data.

The *Ginkgo biloba* extract used preferably contains 20 to 30% of *Ginkgo* flavone glycosides, more preferably 24%, and a mixture of diterpenes/sesquiterpenes preferably ranging between 2 and 10%, and more preferably about 6%.

The *Ginkgo biloba* extract complexed with a mixture of phospholipids, is prepared according to known preparation methods (such as U.S. Pat. Nos. 5,043,323 and 5,202,313).

A crude phospholipid mixture preferably containing 5 to 50% of phosphatidylserine, which improves the bioavailability of the active ingredients, can be used to form the *Ginkgo biloba* complex with phospholipids. According to a preferred aspect of the invention, the phospholipid mixture contains 20% phosphatidylserine.

It has now surprisingly been found that by combining an *Andrographis paniculata* extract with a *Ginkgo biloba* extract complexed with a mixture of phospholipids, preferably containing phosphatidylserine, the neurovascular degenerations typical of Alzheimer's disease, and partly of multiple sclerosis, can be reduced in laboratory animals, enhancing the cognitive capacity after only one week's oral treatment.

The doses of *Andrographis paniculata* extract which have proved effective in the composition range between 0.5 and 2 mg per kilo of body weight, administered one to three times a day. For the *Ginkgo biloba* complex with phospholipids, the dose ranges between 100 and 300 mg per pharmaceutical form, as illustrated in the examples below.

In specific tests, the compositions according to the invention demonstrate the ability to control the progress of neurodegenerative disorders such as Alzheimer's disease and multiple sclerosis.

Moreover, the Applicant has surprisingly found that the compositions described above, when administered in oils rich in ω-3 polyunsaturated fatty acids, demonstrate a further synergic effect between the *Andrographis paniculata* extract and the *Ginkgo biloba* extract complexed with phospholipids.

The composition can be incorporated in the most common pharmaceutical formulations, such as soft or hard gelatin capsules and cellulose capsules, in particular those suitable for containing oils, tablets and suppositories.

The use of cellulose capsules is particularly preferred.

A preferred formulation is the cellulose formulation, wherein the active ingredients of the composition are suspended in vegetable or animal oils rich in ω-3 polyunsaturated fatty acids.

The oils used can be vegetable oils, such as *Linum usitatissimum*, *Oenothera biennis* and *Ribes nigrum* oils and derivatives thereof, or animal oils, such as fish oil, and derivatives thereof.

According to another preferred aspect, 250 mg of *Ginkgo biloba* complex with phospholipids containing phosphatidylserine can be dispersed in the formulation in oil together with 150 mg of *Andrographis paniculata* extract having a 35% andrographolide content.

According to a further aspect, the compositions according to the invention can be administered in conjunction with other substances that possess useful or complementary activity.

The pharmaceutical compositions according to the invention can be formulated according to conventional techniques, such as those described in "Remington's Pharmaceutical Handbook", Mack Publishing Co., N.Y., USA. In particular, the compositions according to the invention will be formulated according to conventional plant ingredient formulation techniques, which require particular care to be taken to avoid interactions with the excipients and the capsule matrices.

EXAMPLES

The examples given below further illustrate the invention.

Example 1

Preparation of Cellulose Capsules with Evening Primrose Oil

| | |
|---|---|
| *Andrographis paniculata* extract (35% andrographolides) | 150 mg |
| *Ginkgo biloba* extract complexed with phospholipid | 250 mg |
| Evening primrose oil | q.s. for 600 mg |

Example 2

Preparation of Cellulose Capsules with Modified Fish Oil

| | |
|---|---|
| Andrographis paniculata extract (35% andrographolides) | 150 mg |
| Ginkgo biloba extract complexed with phospholipid | 250 mg |
| Ethyl eicosapentaenoate | q.s. for 600 mg |

Example 3

Preparation of Hard Gelatin Capsules

| | |
|---|---|
| Andrographis paniculata extract (35% andrographolides) | 150 mg |
| Ginkgo biloba with phosphatidylserine | 150 mg |

Example 4

Effect of Composition (Example 1) on Time of Flight in APPswe/PS1 Double Transgenic Mice The experimental model on which the study was performed is the APPswe/PS1 transgenic mouse.

This animal model expresses the human gene presenilin 1 (delta E9) and the chimeric mouse/human gene of amyloid precursor protein (APP), which in turn contains the Swedish mutation.

It has previously been demonstrated that this animal model is characterised by abnormal amyloid deposition, with progressive memory loss (Borchelt D. et al. Neuron 19, 1997, 939-945), thus demonstrating one of the most predictive models for the study of drugs designed to treat Alzheimer's disease.

Treatment of 20 transgenic mice per group with the composition described in example 1 and the individual ingredients demonstrates that the composition according to the invention significantly reduces memory loss induced by amyloid accumulation in the transgenic mouse, as demonstrated in the Morris water maze paradigm test (Morris R G M, J. Neurosci. Methods 1984; 11:47-60).

In particular, a surprising synergy of action between the ingredients of the composition has been found (Table 1).

TABLE 1

| Group | Time of flight (sec) | % increase |
|---|---|---|
| Normal mouse | 15 ± 2 | — |
| Transgenic mouse | 75 ± 3 | 400 |
| Andrographis paniculata extract | 50 ± 2 | 233 |
| Complex of Ginkgo biloba with phospholipids | 65 ± 3 | 333 |
| Composition according to the invention (Example 1) | 25 ± 2 | 66 |

Example 5

Effect of the Composition (Example 1) on Autoimmune Encephalitis in the Mouse The animal model used to evaluate the products in the treatment of multiple sclerosis is Experimental Autoimmune Encephalomyelitis (EAE) of the mouse. This experimental model is characterised by the onset of focal areas of demyelination of the central nervous system with loss of axonal functionality and progressive ascending paralysis of the hind and fore legs (Iruretagoyena M. I. et al., J. Pharm. Exp. Therapeutics, 312, 366-372, 2005).

Female C57BL/6 mice are injected subcutaneously with 50 µg of $MOG_{35-55}$ peptide (the code MOG identifies myelin oligodendrocyte glycoprotein of the mouse) emulsified in Freund adjuvant (Gibco BRL, JPET # 725128 NY) with the addition of deactivated Mycobacterium tuberculosis H37 RA (Difco Laboratories, Detroit, Mich.). The mice also receive an intraperitoneal injection of 500 ng of Pertussis toxin (Calbiochem La Jolla, Calif.) at the time of sensitisation, and 48 hours thereafter. Clinical signs of the disease appear between 15 and 18 days after sensitisation, and are recorded daily on the basis of the following scores:

0=no signs of EAE
1=limp tail
2=weakness of hind legs or abnormal gait
3=complete paralysis of hind legs
4=complete paralysis of hind and fore legs
5=death The mean clinical data are calculated by adding the daily scores of the mice belonging to the same treatment group, and dividing by the number of mice. Treatment of 20 transgenic mice per group with the composition described in Example 1 and the individual ingredients (commenced 1 week before sensitisation with MOG peptide and continued throughout the experiment) demonstrates that the composition according to the invention significantly reduces all the parameters evaluated, and at the same time demonstrates a surprising synergy of action between the ingredients of the composition (Table 2).

TABLE 2

| Group | Incidence | Score (maximum) | Average of maximum scores |
|---|---|---|---|
| Control | 20/20 (100%) | 5 | 3.9 ± 0.1 |
| Andrographis paniculata extract | 7/20 (35%) | 4 | 2.9 ± 0.1* |
| Ginkgo biloba complex with phospholipids | 4/20 (20%) | 5 | 3.3 ± 0.1 |
| Composition according to the invention (Example 1) | 12/20 (75%) | 2 | 2.2 ± 0.1** |

*$p < 0.05$ Student's t-test
**$p < 0.01$ vs. control

The invention claimed is:

1. A composition for treating a neurodegenerative disease comprising effective amounts of:
   (a) an extract of Andrographis paniculata or pure andrographolide; and
   (b) an extract of Ginkgo biloba complexed with phospholipids.

2. The composition according to claim 1, wherein the extract of Andrographis paniculata contains 20% to 60% of andrographolides, preferably 35%.

3. The composition according to claim 2, wherein the andrographolides are andrographolide, 14-deoxy-11,12-dihydroandrographolide, and neoandrographolide.

4. The composition according to claim 1, wherein the extract of Ginkgo biloba contains from 20% to 30% of Ginkgo bilboa flavone glycosides and from 2% to 10% of a mixture of diterpenes/sesquiterpenes.

5. The composition according to claim 1, wherein the phospholipids comprise phosphatidylserine.

6. The composition according to claim 5, wherein the phosphatidylserine ranges from 5 to 50%.

7. The composition according to claim 1, further comprising one or more vegetable and/or animal oils rich in ω-3 polyunsaturated fatty acids.

8. The composition according to claim 7, wherein the vegetable and/or animal oils are selected from the group consisting of *Linum usitatissimum oil*, *Oenothera biennis* oil, *Ribes nigrum* oil, and fish oil.

9. A method for treating a neurodegenerative disease in a subject in need thereof comprising administering an effective amount of the composition according to claim 1 to said subject.

10. The method of claim 9, wherein the neurodegenerative disease is Alzheimer's disease.

11. The method of claim 9, wherein the neurodegenerative disease is multiple sclerosis.

* * * * *